United States Patent [19]

Kuceski

[11] 4,020,099
[45] Apr. 26, 1977

[54] PURIFICATION OF DIPHENYL TEREPHTHALATE

[75] Inventor: Vincent P. Kuceski, Chicago, Ill.

[73] Assignee: The C. P. Hall Company, Stow, Ohio

[22] Filed: Jan. 27, 1975

[21] Appl. No.: 544,259

Related U.S. Application Data

[63] Continuation-in-part of Ser. No. 269,120, Oct. 10, 1972, abandoned.

[52] U.S. Cl. .......................................... 260/475 PN
[51] Int. Cl.² .................... C07C 69/80; C07C 69/82
[58] Field of Search .................. 260/475 B, 475 PN

[56] References Cited

UNITED STATES PATENTS 3,705,186   12/1972   Naskar et al. ............... 260/475 PN

FOREIGN PATENTS OR APPLICATIONS 1,469,997   2/1967   France ........................ 260/475 B
1,092,899   11/1960   Germany ....................... 260/525

OTHER PUBLICATIONS

Parker, Chemical Reviews, 69, vol. pp. 1–32 (1969).

*Primary Examiner*—Jane S. Myers

[57] ABSTRACT

Diphenyl phthalates are purified by crystallizing them from dipolar-aprotic solvents or solutions of solvents containing such solvents. The phthalate solutions are advantageously, but not necessarily, treated in a carbon column in hydrocarbon solvent without dipolar-aprotic solvents present to remove part of the color and impurities, and then dipolar-aprotic solvents are added to the solution before crystallization to aid in the final removal of color and impurities.

3 Claims, 1 Drawing Figure

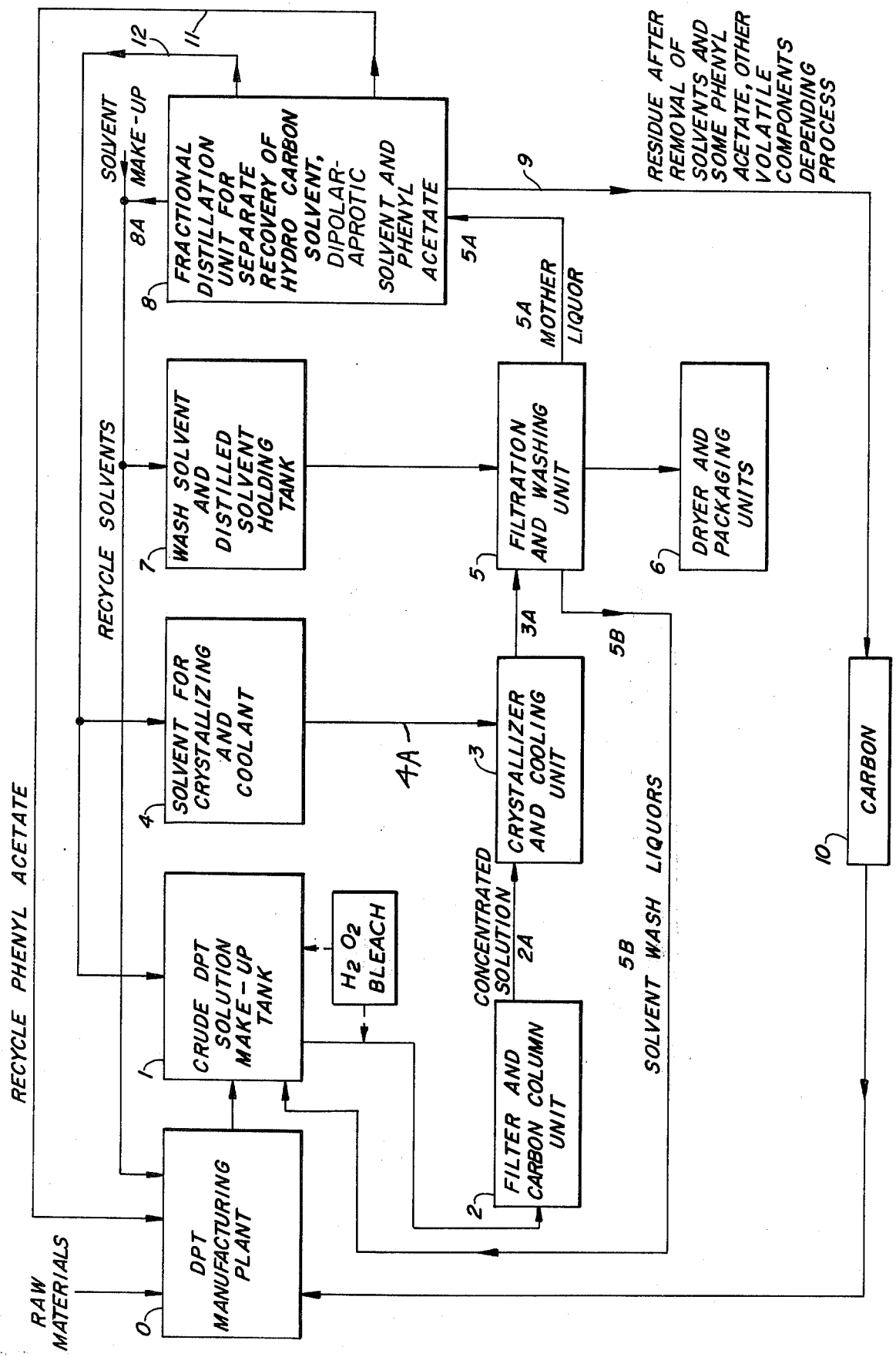

PURIFICATION OF DIPHENYL TEREPHTHALATE

This is a continuation-in-part of application Ser. No. 296,120 filed Oct. 10, 1972, now abandoned.

This invention consists of a new method for the purification of diphenyl terephthalate and other diphenyl phthalate esters and involves batch or continuous methods of production using novel solvent systems.

Diphenyl phthalates are high melting compounds which have had much interest as additives to textiles, especially textiles based on polyesters. They are also contemplated for use in hot melt adhesives, sealants, dye carriers, as reaction solvents, in dry metal lubricant systems, paints, heat transfer fluids, etc.

In the prior art diphenyl phthalate (DPT) has been made by the following reactions:

Phenyl acetate + dialkyl phthalate $\xrightarrow[heat]{catalyst}$ diphenyl phthalate + alkyl acetate in which the alkyl group contains 1 to 8 to 12 or more carbon atoms.

Other reactions which can be used in making the product are as follows:

Phthalic acid + phenol $\xrightarrow{catalyst}$ Diphenyl phthalate + HOH

Phthaloylyl chloride + phenol → Diphenyl phthalate + HCl

Phthalic acid + phenyl chloride → Diphenyl phthalate + HCl

The reactions usually require certain catalysts and heat and some of the best catalysts are based on organic-titanium compounds, tin compounds, and combinations with other metals. However, these catalysts generate colors such as deep red which cannot be completely removed by recrystallization from solvents, by the use of adsorbing agents, such as activated carbon or bleaching earth, or even by repeated recrystallization. This is discussed in British Pat. No. 1,205,542.

I have found solvent systems the use of which results in pure water-white diphenyl tere-, meta- and ortho-phthalates, with or without the use of carbon as decolorizing agent. A solution may be treated to a preliminary decoloring step such as by treating with decolorizing carbon particles, hydrogen peroxide or the like, although this may not be necessary.

In my solvent system, I have found that certain solvents of the class known as dipolar-aprotic solvents are good solvents and co-solvents for the purification of diphenyl phthalates obtained by one of the above mentioned processes. A good discussion of these solvents is given in *Chemical Reviews*, Vol. 69, No. 1, Feb., 1969, pages 1–32.

Dipolar-aprotic solvents are, by definition, weak or non-hydrogen-bond donating, and have relatively strong dipoles. They have a dielectric constant greater than substantially 15. They are hydrogen acceptors and some may be powerful bases, although most are considered neutral. They have strong interactions with solutes which are strong hydrogen bond donors. They also, more importantly perhaps, have the ability to complex with many metals and their derivations. The following are illustrative:

| | |
|---|---|
|  | in which R is hydrogen, an alkyl group of 1 to 10 carbon atoms, phenyl, tolyl or xylyl, and $R^1$ and $R^2$ are hydrogen or an alkyl group of 1 to 4 carbon atoms. |
| $CH_3 . SO . CH_3$ | Dimethyl sulfoxide. |
| $CH_3 . SO_2 . CH_3$ | Dimethyl sulfone. |
|  | in which R and R' are the same or different and are alkyl groups of 1 to 4 carbon atoms. |
| R—C—N | in which R is an alkyl group of 1 to 6 carbon atoms or phenyl. |
| $R—(CN)_2$ | in which R is an alkylene group of 1 to 4 carbon atoms. |
| R R' R''—O=P—O | in which R, R' and R'' are the same or different and are alkyl groups of 1 to 4 carbon atoms. |
| $R_2N-\overset{\overset{O}{\|}}{\underset{\underset{NR_2}{\|}}{P}}-NR_2$ | in which the R's are methyl or ethyl. |
| 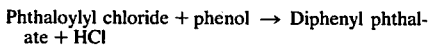 | in which R and R' are the same or different and are phenyl or alkyl groups of 1 to 4 carbon atoms. |
| $R'_2NOC—(CH_2)_{2-4}—COOR$ | N,N'-dialkyl carboxylic acid ester in which the alkyl groups are the same or different and contain 1 to 4 carbon atoms. |
| 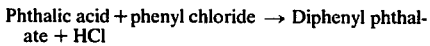 | N-alkyl-2-pyrrolidone in which the alkyl group contains 1 to 4 carbon atoms. |
| (CH₂) \<C=O / O | alkylene carbonate in which the alkylene group contains 2 or 3 carbon atoms. |

Representative solvents follow:

| | |
|---|---|
| Dimethyl formamide | Dimethyl propionamide |
| Dimethyl acetamide | Diethyl caproamide |
| Hexamethyl phosphoramide | Dipropyl caprylamide |
| Acetone | Dibutyl capramide |
| Nitromethane | Dimethyl benzamide |
| Nitrobenzene | N,N'-Dimethyl glutaramide-methyl ester |
| Acetonitrile | Triethyl phosphate |
| Benzonitrile | Tributyl phosphate |
| N-Methyl-2-pyrrolidone | Dibutyl ketone |
| Dimethyl sulfone | Methylbenzoate |
| Dimethyl sulfoxide | Dimethyl glutarate |
| Dipolar-aprotic | Propylene carbonate |

As the examples show, most of these solvents have an atom which acts as an electron sink and this atom becomes negatively charged.

Ketones and esters in this group have the weakest dipolar-aprotic activity. This type of activity usually works best where oxygen is attached to an atom such as nitrogen, sulfur, or phosphorous; they can exhibit several valence states, and because the outer shell of excess electrons can displace some electronegativety toward the oxygen atom, thus creating an electronegative charge which can attract protons and positively charged groups or atoms. This behavior also relates to its ability to complex with many metals, their salts, esters, and other derivatives.

To prove the superiority of the solvent systems of this invention, a comparison was made between purity obtained by the process of the invention and that obtained by a process of the present state of the art.

EXAMPLE 1A

This process is an example of the present state of the art (British Pat. No. 1,205,542):

| | |
|---|---|
| Dimethyl terephthalate | 595 parts |
| Phenyl acetate | 1000 parts |
| Activated carbon | 16 parts | are melted together under an inert gas in a flask provided with a stirrer, thermometer, inert gas inlet, and fractionating column and heated with stirring for 10 minutes at 150° C. while a current of inert gas is passed through the apparatus. 4.0 parts of tetrabutyl titanate are then added and the reaction started at about 185° C. The reaction was finished in about 3 hours with a final temperature of 235° C. It was then poured hot into 3 liters of xylene containing 16 grams of activated carbon, and the solution was heated to dissolve the DPT while the solution was filtered to remove the carbon. The solution was then cooled to crystallize DPT and a yellow crystal was obtained which was washed with fresh xylene solvent and dried. The washed crystal was yellow in color and was assigned 4 on the color value rating scale described below:

COLOR STANDARDS

Note: A series of color standards were made up using the colors produced by the reaction because the color bodies appearing in the crystals are the same character in tint and color as the color appearing in the filtrate. Thus, small amounts of the color dissolved in the xylene filtrate from the first crystallization was added to xylene to produce a series of colors which range from an almost water white tint (No. 1) to a red-yellow (No. 7). A reading of 0 is given to a water white sample. Thus, the color standards and values assigned are:

| Color Value | Description of Color |
|---|---|
| 0 | Water white, APHA 10 or less |
| 1 | Near water white to light yellow, APHA 50 or less |
| 2 | Light yellow, Gardner 2 |
| 3 | Yellow, Gardner 3 |
| 4 | Dark Yellow, Gardner 6 |
| 5 | Reddish Yellow, Gardner 9 |
| 6 | Amber, Gardner 10–11 |
| 7 | Red, Gardner 12 |

The test is made on the initial color of the melted sample and on the color of the melted sample when held under an inert atmosphere of nitrogen for 6 hours at 220° C. This heat test is a reliable method which shows up any tendency to produce color bodies. A reading of 3 or under after 6 hours at 220° C. is satisfactory. An initial color reading of 2 or under before the heat test is usually satisfactory.

In the example above, as already stated, the initial color of the melted crystal was 4, and the color after the heat test was over 7. Thus, one recrystallization was not satisfactory. Only after 3 more crystallizations with xylene was satisfactory crystal product obtained on initial color; but, even then, the sample, when subjected to the 6 hour heat test, failed with a color value of 4, whereas 3 is the most color that can be tolerated in commercial practice.

EXAMPLE 1B

The procedure for making the DPT (diphenyl terephthalate) is the same but no carbon is used in the reaction mixture or in the xylene solvent solution after the reaction. The difference was in the composition of the solvent. A solvent pair was used with the following composition:

88% xylene
12% dimethylformamide (DMF)

When this solvent pair was used at a ratio of 8 parts to 1 part of crude DPT, a crystal was obtained after hot filtration which was light yellow in color after washing with fresh xylene solvent. A color value of 2 was assigned to the crystal.

Upon recrystallization of the light yellow crystal with fresh xylene-DMF solution with the composition given above at a ratio of 7 to 1 and washing with fresh xylene, a white crystal was obtained with a crystal color value of 1. The 6-hour test at 220° C. gave a color value of 1 showing that this material was quite pure and stable. This example proved that the use of the dipolar-aprotic solvent DMF gave a far superior crystal product in 2 crystallizations from the DMF-xylene mixture whereas even 3 crystallizations from xylene alone as in Example 1A did not yield a satisfactory product.

EXAMPLE 2

In this example, we show a procedure which utilizes carbon as a de-colorant in which the crude material produced by the reaction of phenyl acetate with dimethyl terephthalate, using tetrabutyl tin catalyst in the same ratio as Example 1B, is first dissolved in xylene by heating 8 parts xylene to 1 part of crude DPT to a temperature of 130° C. 300 ml of this solution is filtered and then passed through a column of granular carbon with dimensions of 1 inch × 12 inches at the rate of 1 linear inch per minute. The color of the liquid after passing through the column was yellowish. The yellowish liquid solution resulting from passing through the column was divided into 2 equal parts which were treated as follows:

Part 1 was cooled to 35° C. and crystallized, filtered, and the crystal product washed with xylene to give a crystal product with a color value of 1. Upon heating 6 hours at 220° C., the color value deteriorated to 4. However, the product compared very favorably with the product obtained previously in Example 1A when 3 crystallizations and washings were necessary.

Part 2 To 1200 parts solution was added 120 parts of hot DMF and the solution cooled to 35° C. as before and the crystals filtered off and washed with fresh xylene. The resulting crystals were snow white and had a color value of less than 1. Upon heating 6 hours at 220° C., the molten product still had an excellent color value of 1.

The above examples show that even after column carbon treatment, the special solvent treatment was needed to give a color-stable product.

EXAMPLE 2B

In this example we show the preparation of diphenyl metaphthalate. The same proportions of phenyl acetate and dimethyl metaphthalate are used as in the examples making the diphenyl terephthalate.

Thus, 595 parts of dimethyl metaphthalate and 1000 parts of phenyl acetate are heated and processed exactly as in Example 1A. However, the reaction took place over a somewhat longer period of time.

One-half the crude product was crystallized twice and washed twice with xylene from a solution of 20% nitrobenzene and and 80% xylene to yield a product with a melting point of 139°–140° C. with an initial color value of 1 and a heat stability color value of 3. Thus, the product was satisfactory for all known commercial uses.

When the other half of the crude product was recrystallized twice from xylene, with washes between crystallizations as done above, a product was obtained with a melting point of 139°–140° C. but the initial color value was 4 and the heat stability test gave a color value of 6.

Thus, the above example shows that diphenyl metaphthalate is also purified better in the dipolar-aprotic solvent than in a hydrocarbon solvent alone.

EXAMPLE 2C

The above experiment was repeated exactly in every detail in the production of ortho-phthalate and the results obtained using the dimethyl sulfoxide dipolar-aprotic solvent were superior than when hydrocarbon solvent toluene was used. Although toluene was somewhat more efficient than xylene, it, too, failed to produce satisfactory material in two crystallizations.

EXAMPLE 3

In a plant run made in 55-gallon stainless steel reactor equipped with agitator, reflux condenser, cooling-heating coils, and a receiver for by-product methyl acetate was placed the following:

| | |
|---|---|
| Dimethyl terephthalate (DMT) | 205 lbs. (0.91 moles) |
| Phenyl acetate | 325 lbs. (2.4 moles) |
| Recovered phenyl acetate (from a previous batch) | 30 lbs. (20 lbs. phenyl acetate) |
| Catalyst tetrabutyl titanate | 1.7 lbs. |

This mixture was dried by heating to 150° C. before the catalyst was added. It was then heated slowly to about 380° F. and, at this temperature, by-product methyl acetate began to distill off very rapidly. The temperature was then cut back in order to prevent the co-distillation of phenyl acetate with the methyl acetate by-product. After about 8 hours the temperature began to increase showing that the reaction was nearing completion. The final temperature attained was 460° F. after 1 more hour of reaction.

Obtained 328 lbs. of crude diphenyl terephthalate (DPT), containing unreacted phenyl acetate, half esters of DMT, and impurities. This material was used in subsequent purification experiments.

The crude product obtained above was dissolved in various classes of solvents at substantially the lowest temperature effecting solution, and crystallized to determine the yield and purification efficiency. Table I gives the results obtained and in each case the solvent-solute ratio was 7 to 1.

TABLE I

| Solvent Class | Special Solvent | Crystallization First % Yield | First Color Value | Second % Yield | Second Color Value |
|---|---|---|---|---|---|
| Amide | Dimethyl formamide (DMF) | 57 | 1 | 78 | <1 |
| Amide | Dimethyl acetamide (DMA) | 57 | 1 | 92.5 | <1 |
| Amide | N,N-Dimethyl glutarate methyl ester | 66 | 2 | 90 | <1 |
| Amide | N,N'-Dimethyl benzamide (DMB) | 60 | 2 | 60.3 | <1 |
| Amide | N-Methyl pyrrolidone (NMP) | 48.5 | 1 | 56 | 2–3 |
| Amide | N-Methyl valeramide | 55 | 3 | 65 | 2 |
| Amide | N,N'-Dimethyl propionamide | 58 | 2 | 80 | 1 |
| Amide | N,N'-Dimethyl caproamide (HALLCOMID M-6) | 58 | 2 | 75 | 1 |
| Amide | HALLCOMID M 8-10 (N,N'-Dimethyl capryl-capra-amide) | 56 | 2 | 75 | 1 |
| Misc. Nitrogen | Acetonitrile | — | — | — | — |
| Misc. Nitrogen | Nitrobenzene | 55 | 2 | 80.4 | <1 |
| Aliphatic Chloride Solvent | Methylene chloride | Solubility too low. | | | |
| Aliphatic Chloride Solvent | 1,1,1-Trichlorethane | Solubility too low. | | | |
| Sulfur | Dimethyl sulfoxide (DMSO) | 64.5 | 4 | 91.5 | <1 |
| Sulfur | CS$_2$ | Solvent too volatile. | | | |
| Aliphatic Hydrocarbon | Mineral Spirits | 60 | 5 | 90 | 4 |
| Aromatic Hydrocarbon | Xylene | 66 | 4+ | 90 | 3+ |
| Aromatic Hydrocarbon | Toluene | 65 | 4 | 91 | 3 |
| Aromatic Hydrocarbon | Benzene | 62 | 3+ | 90 | 3 |
| Phosphate | N,N',N'',-Hexamethyl phosphoramide | 65 | 2 | 85 | 1 |
| Phosphate | Tributyl phosphate | 65 | 2 | 80 | 1 |
| Ester | Dimethyl glutarate (DMG) | 64 | 3 | 85 | 3 |

TABLE I-continued

| Solvent Class | Special Solvent | Crystallization | | | |
|---|---|---|---|---|---|
| | | First | | Second | |
| | | % Yield | Color Value | % Yield | Color Value |
| Alcohol | Butyl alcohol | No crystal | — | No crystal | — |
| Alcohol | Hexanol | No crystal | — | No crystal | — |

It should be noted upon inspection of the data that the solvents with the best ability to remove color contaminants are (1) the nitrogen-containing compounds, specifically the amides, phosphoramides, nitrobenzenes and (2) the sulfur compound such as DMSO.

The aromatic hydrocarbon compounds, aliphatic hydrocarbon compounds, and esters, ketones and chlorinated compounds were ineffecient in removing impurities or were not a good solvent for diphenyl terephthalate. Acetonitrile appeared to have potential but because of its low boiling point, not enough DPT went into solution. Higher molecular weight nitriles would probably be satisfactory.

The dipolar-aprotic solvents may be used alone or in combination with other solvent which is a hydrocarbon, such as benzene, toluene, xylene or aliphatic hydrocarbon solvents, such as pentane, heptane, hexane, mineral spirits, kerosene, etc. The ratio of the parts by weight of the other solvent to the dipolar-aprotic solvent can be as low as 1:1 or as high as 20:1. Preferably a ratio of from 3:1 to 10:1 is used in order to get pure material with a minimum number of recrystallizations.

In our tests, we show that from 6 to 10 or 20% is usually needed to accomplish the intended purification effect when DMF is used in xylene. More DMF can be used with increasing effect, but the purification efficiency begins to level off at a weight ratio of DMF to xylene of about 50%.

EXAMPLE 4

In this example we show a procedure which yields excellent crystals of DPT by a variation in the process of manufacture. This example shows how crystallization can be effected without external cooling and consequent caking of the crystallizers. The steps in this process include:

1. Solution of crude DPT in dipolar-aprotic solvent and aromatic or aliphatic hydrocarbon solvent (mixtures at low solvent to solute ratios, i.e., 1:1 to 5:1). Thus, a solution at a ratio of solvent to DPT of 3.5 to 1.0 at a temperature of 90°–110° C. is first made. Then,
2. 3.5 parts cold solvent are added to the solution with good agitation to crystallize DPT out of solution rapidly.
3. Filtering such crystals off and washing with fresh xylene or hexane.

This method eliminates the need for a separately cooled crystallizer. Such crystallizers frequently must be operated so that the cooling applied to the vessel jacket is not too fast, otherwise, crystals are formed on the inside surface which further complicates the process because heat transfer is impaired. Such crystals when of substantial size may take from several hours to 20 hours or more to cool at a rate which does not cause the growth of a crust of crystals on the inner wall or jacket. Ideally, such cooling should be rapid, internal, and efficient in order to prevent crystal growth on cooled or refrigerated parts. It is true that scraped-wall crystallizers are also employed to prevent the occurence of the problem mentioned above, but this method is also not entirely satisfactory. One of the objects of this invention is to eliminate the need for costly crystallizers, special agitated vessels, heat exchangers, and specialized coolers and other equipment. By the process of this invention cooling and crystallizing is provided inexpensively, instantaneously, and efficiently.

The sequence in which the solutions are mixed is also important. It is important to determine if (1) the solution should be added to the solvent to cool down the crystallizing solution, or (2) alternatively, the solvent is added to the solution to cool down the solution. We believe the latter is the most efficient and the sequence of choice, and in the example below, we prove the value of this sequence:

EXAMPLE 5

In this experiment, 1000 parts of crude DPT is dissolved in a special solvent 3000 parts containing 75% by weight of xylene and 25% DMF and the solution filtered while hot (120° C.) to remove insoluble impurities. The solution was then divided into 2 parts of approximately 2000 grams each.

PART 1

One part of 110° C. was poured into 2000 grams of xylene, which was at a temperature of 27° C., with good agitation in a period of 5 minutes, whereupon the mixed solution rapidly warmed to a final temperature of 80° C.

At this point, about 70% of the crystal crop appeared. Further cooling to 50° C. by external means crystallized the remainder giving a yield of 300 grams of purified DPT after washing with fresh xylene solvent and drying. Upon analysis, we find that by this method we obtained a crystal with an initial color value of 2 and a melting point of 195° C.

PART 2

PREFERRED PROCEDURE FOR COOLING 2000 grams containing 500 grams of crude DPT at 115° C., was agitated rapidly and, while agitating, 2000 grams of xylene was added over a period of 5 minutes. The temperature cooled rapidly to about 80° C. whereupon crystallization began when about 70% of the xylene solution was added. As more xylene solvent was added, more crystals separated until all the xylene has been added. External cooling was then applied to cool to 50° C. and then the material was filtered and the filter cake washed with xylene to give a yield of 303 grams after drying.

The difference of only 3 grams in yield is well within the experimental error. This material crystallized by the second method had a melting point of 197°–98° C. and a color value of 2. Pouring the hot solution of DPT into hydrocarbon solvent, is a better method of obtaining a higher melting product, than pouring the hydrocarbon solvent in the hot solution of DPT. The yield is as good or better than the reverse method.

In the above experiment, external cooling could be easily applied without a crystalline crust appearing on the walls of the container because approximately 95% of the material had already crystallized. On further cooling, very little more material crystallized.

The above cycle was repeated with the DPT crystals obtained from Part 1 and Part 2. Thus, 300 grams of DPT crystals from Part 1 were dissolved in 1000 grams of a mixture of 750 grams of xylene and 250 grams of DMF and the mixture was cooled to a temperature just above the temperature of crystallization (about 115° C.) and then this was poured rapidly into cool (20° C.) xylene (2000 grams) which was rapidly agitated. Upon mixing in some of the solution of DPT into the cool xylene some crystal appeared immediately and crystallization continued as more solution was added to the cool xylene until all was added. The final temperature was 40° C. and external cooling was unnecessary. The filtered crystal was washed with xylene and dried yielding 270 grams of material having a melting point of 198°–99° C. and a color value of 1.

The reverse crystallization method was again carried out with the 303 grams obtained from the first crystallization from Part 2. The same type and volume of solvent was used. Thus, 303 grams of Part 2 crystal dissolved in 1000 grams of solvent composed of 750 grams xylene and 250 grams of DMF were prepared and cooled to 115° C. Then 2000 grams of xylene at 20° C. was poured over a period of 5 minutes into the well-agitated solution of DPT. No crystallization appeared until the temperature dropped to about 65° C. when about half the xylene solvent had been added. As more xylene was added, crystallization slowed the cooling and a final temperature of 45° C. was reached when all the xylene solvent had been added. The crystal crop obtained the usual way after washing and drying weighed 268 grams and had a melting point of 199°–200° C. and a color value of 1.

Thus, Part 2 seems more efficient as a method for obtaining a pure crystal as shown by melting point. Upon subjecting the crystal from Part 1 and Part 2 to the heat stability test, the crystal from Part 2 gave a color value of 2 and the crystal from Part 1 gave a color value of 3. The superiority of Part 2 seems to be verified.

EXAMPLE 6

The diagram in FIG. 1 illustrates the commercial adaptation of this invention wherein superior products are produced.

Raw materials are fed to the manufacturing plant where diphenyl terephthalate (DPT) is made. The DPT may be made by any commercial method. Thus, it may be made by (1) the reaction of phenyl acetate with dimethyl terephthalate, (2) the reaction between phenol and the diacid chloride of terephthalic acid, (3) by the reaction of phenol and terephthalic acid, or (4) by the reaction between phenyl chloride and terephthalic acid, or by any other methods producing diphenyl terephthalate.

The crude, hot DPT from the DPT manufacturing plant 0 is fed to tank 1 where wash solvent and/or make-up recycled distilled solvent is used to make a solution of dipolar-aprotic solvent and other solvent at a ratio of from 2 to 1, to 10 to 1 or more. This hot solution is then filtered to remove insoluble impurities and passed through a carbon column to remove color and other impurities in column 2. The solution is then passed to crystallizer unit 3, which may be a batch or continuous unit, and at the same time sufficient cold solvent (dilute solvent) is added in sufficient amount from tank 4 by line 4A to cool the whole solution to a temperature of from 25° to 50° C. or to a temperature which will allow the precipitation of substantially all the DPT present in the solution. The precipitate slurry is then pumped or sucked by vacuum by line 3A to continuous filter unit 5 which continuously filters and washes the DPT crystals with fresh and recycled solvent from tank 7. Wash liquors from unit 5 are recycled by line 5B without distillation to tank 1 for use in making crude DPT solution.

The mother liquor from the crystal DPT passes by line 5A to a distillation unit 8 which fractionates the solvent solution into 2 fractions: the hydrocarbon solvent, if it is used, and the dipolar-aprotic solvent. The hydrocarbon solvent is removed by line 8A where it may be used for recycle to tank 1 and 7 for solution and washing respectively, or it may be used in tank 4 as part or all of the cooling and crystallizing solvent.

Line 12 is used to transfer fractionated dipolar-aprotic solvent to tank 1 or 4. It is not usually used in the wash solvent. The fractionated hydrocarbon solvent is advantageously used as indicated for the solution of DPT before treatment in the carbon column.

The residue which contains unprecipitated DPT, half esters of DPT, unreacted dimethyl terephthalate, and phenyl acetate, if not fractionated and recovered separately, or other raw materials from other processes previously mentioned used in manufacture, is recycled by line 9 to the DPT manufacturing plant. The residue, which is quite dark, may be passed through used carbon from column 2 in column 10 in order to remove concentrated impurities. Line 11 may be used to cut out phenyl acetate if phenyl acetate is fractionated and return to the DPT manufacturing unit.

It should perhaps be again emphasized that without the solvents of this invention, a more expensive and elaborate purification system would have to be devised requiring double or triple recrystallization with 2 or 3 filtration and wash units, and much more solvent storage and heat and cooling requirements. The solvents of this invention allow the construction of a purification unit at a cost of about one-half of the cost of a plant which would use less efficient solvents.

Although the examples are limited to diphenyl phthalates, the process of this invention can be extended to the treatment of any other aromatic diester containing impurities which are difficult to remove.

The process may be operated batch-wise, continuously, batch-wise with recycle of solvents and solvent residue, continuously with recycle of solvent and solvent residue, or any combination of the above.

The invention is illustrated in the examples given and in the claims:

I claim:

1. The method of purifying a diphenyl phthalate which comprises crystallizing it from a solution which contains a dipolar-aprotic solvent and a hydrocarbon solvent wherein the ratio of the hydrocarbon solvent to the dipolar-aprotic solvent is 1:1 to 20:1, the dipolar-aprotic solvent being selected from the class consisting of
a. amides of the formula

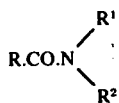

in which R is
hydrogen, an alkyl group of 1 to 10 carbon atoms, phenyl, tolyl and xylyl; and $R^1$ and $R^2$ are from the class consisting of hydrogen and alkyl groups of 1 to 4 carbon atoms;
b. dimethyl sulfoxide;
c. nitrile of the formula R—C—N in which R is from the class consisting of alkyl groups of 1 to 6 carbon atoms and phenyl;
d. phosphates of the formula RR′R″-O=P-O in which R, R′ and R″ are the same or different and are alkyl groups of 1 to 4 carbon atoms;
e. phosphoramides of the formula

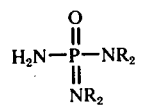

in which the R's are methyl or ethyl;
f. N,N′-dialkyl carboxylic acid esters of the formula $R'_2NOC-(CH_2)_2$ to $_4$-COOR in which the alkyl groups are the same or different and contain 1 to 4 carbon atoms; and
g. nitrobenzene.

2. The method of claim 1 in which the ester is diphenyl terephthalate.

3. The method of claim 1 in which the ester is a diphenyl phthalate and the solvent has the formula $R.CO.NR'_2$ in which R is hydrogen, an alkyl group of 1 to 10 carbon atoms, phenyl, tolyl or xylyl and each R′ is hydrogen or an alkyl group of 1 to 4 carbon atoms.

* * * * *

UNITED STATES PATENT OFFICE
CERTIFICATE OF CORRECTION

Patent No. 4,020,099          Dated April 26, 1977

Inventor(s) Vincent P. Kuceski

It is certified that error appears in the above-identified patent and that said Letters Patent are hereby corrected as shown below:

Column 2, line 49, cancel "Dipolar-aprotic"

Signed and Sealed this second Day of August 1977

[SEAL]

Attest:

RUTH C. MASON
*Attesting Officer*

C. MARSHALL DANN
*Commissioner of Patents and Trademarks*